(12) United States Patent
Enzien et al.

(10) Patent No.: US 8,012,758 B2
(45) Date of Patent: Sep. 6, 2011

(54) METHOD OF MONITORING MICROBIOLOGICAL ACTIVITY IN PROCESS STREAMS

(75) Inventors: Michael V. Enzien, Lisle, IL (US); Laura E. Rice, Long Beach, CA (US); Stephen B. Ashton, Chester (GB)

(73) Assignee: Nalco Company, Naperville, IL (US)

( * ) Notice: Subject to any disclaimer, the term of this patent is extended or adjusted under 35 U.S.C. 154(b) by 879 days.

(21) Appl. No.: 11/675,726

(22) Filed: Feb. 16, 2007

(65) Prior Publication Data
US 2008/0199901 A1 Aug. 21, 2008

(51) Int. Cl.
*G01N 35/08* (2006.01)
*C02F 1/00* (2006.01)
*G01N 33/00* (2006.01)
*G01N 21/00* (2006.01)

(52) U.S. Cl. ............... 436/52; 436/43; 436/62; 436/138; 422/62; 422/68.1; 422/73; 422/79; 210/739; 210/143; 210/198.1; 435/29; 435/32; 435/287.1

(58) Field of Classification Search .......................... None
See application file for complete search history.

(56) References Cited

U.S. PATENT DOCUMENTS

| | | | |
|---|---|---|---|
| 3,510,106 A | 5/1970 | Stack, Jr. | |
| 3,510,406 A | 5/1970 | Stack, Jr. | |
| 3,731,522 A | 5/1973 | Mikesell | |
| 5,190,728 A | 3/1993 | Robertson et al. | |
| 5,281,537 A | 1/1994 | Robertson et al. | |
| 5,552,319 A | 9/1996 | Yang et al. | |
| 5,576,481 A | 11/1996 | Beardwood | |
| 5,807,699 A | 9/1998 | Nason et al. | |
| 6,475,394 B2 | 11/2002 | Xiong et al. | |
| 7,078,201 B2 | 7/2006 | Burmaster | |
| 2005/0009192 A1 | 1/2005 | Page | |

OTHER PUBLICATIONS

Ludensky, M.L., "An automated system for biocide testing on biofilms", *Journal of Industrial Microbiology & Biotechnology*, vol. 20, 1998, pp. 109-115.
N-CON Systems Co., Inc., "N-CON Systems BIOSCAN On-line Toxicity or Treatment Inhibition Monitor," On-line Bulletin, Sep. 2004 (date that webpage was updated), 4 pages.
U.S. Appl. No. 11/943,184—Office Action with Mail Date of Mar. 18, 2010.
U.S. Appl. No. 11/943,162—Office Action with Mail Date of Mar. 18, 2010.
International Search Report.
International Search Report, Jul. 22, 2008.
International Search Report for International Appln. No. PCT/US08/53976.
International Search Report for International Appln. No. PCT/US08/53976, Jul. 22, 2008.

*Primary Examiner* — Jill Warden
*Assistant Examiner* — Neil N Turk
(74) *Attorney, Agent, or Firm* — Benjamin E. Carlsen; Michael B. Martin

(57) ABSTRACT

An apparatus and method for monitoring microbiological activity in a process stream by measuring dissolved oxygen is disclosed. Bulk microbiological activity and surface associated biological activity are measured using this apparatus and method.

6 Claims, 10 Drawing Sheets

METHOD OF MONITORING MICROBIOLOGICAL ACTIVITY IN PROCESS STREAMS

FIELD OF THE INVENTION

This invention pertains to an apparatus for monitoring microbiological activity in process streams and a method of monitoring microbiological activity in process streams.

BACKGROUND

Microbial growth in commercial water systems can lead to spoilage and surface-fouling. If growth is not adequately controlled, spoilage can lead to offensive odors and reduced function of additives (e.g. microorganisms can produce catalase that hydrogen peroxide uses to enhance brightness and can produce cellulases that can impact fiber strength). If surface-fouling is not adequately controlled, resulting biofilms can interfere with heat-exchange, and in the case of papermaking systems biofilms can create a need to slow down the manufacturing process, shut-down the process to clean these deposits from surfaces, or might slough from surfaces causing holes or spots in the finished paper or board product. Therefore, such waters are treated with biocides to control microbial growth and prevent related problems.

Because spoilage and biofilm-formation contribute to different problems in industrial water systems and planktonic and sessile bacteria respond differently to biocontrol measures, there is a need to monitor the impact of biocontrol programs on these different modes of microbial growth.

Standard techniques typically used to monitor such water systems include standard plate count techniques. These techniques require lengthy incubation periods and do not provide adequate information for pro-active control and prevention of problems related to microbial growth. More recently, adenosine triphoshphate (ATP) measurements have been used as a means of pro-active control. However, the reagents are costly and small volumes are sampled from large water systems. Data collection is also infrequent, leading to significant gaps in data. Therefore, this approach provides limited information on the status of microorganisms in the system of interest. In addition, these approaches are typically used to monitor planktonic bacteria. Although in some cases, surfaces might be swabbed and analyzed in order to quantify biofilm bacteria. These approaches are very tedious and time-consuming.

Dissolved oxygen (DO) probes have been used to measure microbial activity in fluids, as it is well known that microbial activity and aerobic metabolism leads to a decrease in dissolved oxygen concentrations. U.S. Pat. Nos. 5,190,728 and 5,282,537, issued to Robertson et al., disclose a method and apparatus for monitoring fouling in commercial waters utilizing DO measurements. However, the approach requires the use of nutrient additions to differentiate biological from non-biological fouling and there is no mention of how the probe is refreshed for further measurements after the probe surface has fouled. In addition, the approach disclosed requires a means of continuously supplying oxygen.

The standard Clark style electrochemical DO probe has many limitations such as: chemical interferences ($H_2S$, pH, $CO_2$, $NH_3$, $SO_4$, $Cl^-$, $Cl_2$, $ClO_2$, MeOH, EtOH and various ionic species), frequent calibration and membrane replacement, slow response and drifting readings, thermal shock, and high flow requirements across membranes. A new type of dissolved oxygen probe, which has recently been made commercially available by a number of companies (e.g., HACH, Loveland, Colo.), overcomes nearly all of these limitations so that DO can be measured on-line in process waters. This new DO probe (LDO) is based on lifetime fluorescence decay where the presence of oxygen shortens the fluorescence lifetime of an excited fluorophore. The fluorophore is immobilized in a film at the sensor surface and the excitation is provided with a blue LED.

U.S. Pat. Nos. 5,698,412 and 5,856,119, both issued to Lee et al., disclose a method for monitoring and controlling biological activity in fluids in which DO is measured in combination with pH to measure transitions in metabolic behavior, specifically related to nutrient/substrate depletion.

There remains a need for reliable and convenient methods to monitor planktonic and biofilm bacteria in commercial waters, which ensure that biocontrol programs adequately control spoilage and problematic biofilms. These methods should be reagentless to allow measurement of microbial activity in conditions representative of those in the ambient environment (minimal modification). These methods should be automated and should allow for remote control of the monitor, remote access to the data, and remote or automated feed-back control of the biocontrol programs. Ideally, these methods would differentiate microbial activity on surfaces from bulk water activity in order to ensure that biocontrol programs adequately address the increased challenges typically faced when trying to control microorganisms in biofilms. Furthermore, these methods would provide information on the nature of the deposits (biological or non-biological) to ensure that appropriate control measures are applied.

SUMMARY OF THE INVENTION

The present invention provides an apparatus for measuring microbiological activity in a process stream comprising: (a) a flow cell containing a plurality of openings, wherein at least one opening is a flow cell inlet for fluid drawn from said process stream and at least one opening is a flow cell outlet for fluid exiting said flow cell; (b) a DO probe attached to one of said openings; (c) optionally an ORP probe attached to one of said openings; (d) a cleaning device attached to one of said openings; (e) optionally a first conduit attached to the flow cell inlet; (f) optionally a second conduit attached to the flow cell outlet; and (g) optionally a valve associated with said flow cell.

The present invention also provides for a method for monitoring bulk (total) microbiological water activity in a process stream comprising: (a) connecting an apparatus to a process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally an ORP probe attached to one of said openings, optionally a cleaning device attached to one of said openings, optionally a first conduit attached to the flow cell inlet, optionally a second conduit attached to the flow cell outlet, and optionally a valve associated with said flow cell; (b) drawing fluid from said process stream into said flow cell; (c) opening the valve of said apparatus to allow fluid to be drawn into said flow cell; (d) measuring at least once the DO concentration of said process stream with said DO probe, and wherein prior to each measurement the surface of said DO probe is cleaned; (e) closing the valve of the apparatus to prevent fluid from being drawn into said flow cell; (f) measuring at least once the DO concentration of the fluid inside the apparatus with said DO probe and wherein prior to each measurement the surface of the DO probe is cleaned; (g) calculating a Δ DO reading between step (d) and step (f); and (h) correlating at least said Δ DO value in step (g) with microbiological bulk (total) activity in said process stream.

The present invention also provides for a method for measuring surface associated microbiological activity in a process stream comprising: (a) connecting an apparatus to a process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally an ORP probe attached to one of said openings, optionally a cleaning device attached to one of said openings, optionally a first conduit attached to the flow cell inlet, optionally a second conduit attached to the flow cell outlet, and optionally a valve associated with said flow cell; (b) drawing fluid from said process steam into said flow cell; (c) opening the valve of said apparatus to allow fluid to be drawn into said flow cell; (d) measuring at least once the DO concentration of said process stream with said DO probe, and wherein said DO probe is not cleaned prior to each measurement; (e) cleaning the surface of said DO probe; (f) measuring at least once both the DO concentration of the fluid inside said apparatus with said DO probe and optionally wherein prior to each measurement said DO probe surface is cleaned; (g) calculating a Δ DO reading between step (d) and step (f); and (h) correlating at least said Δ DO in step (g) with surface associated microbiological activity.

The present invention further provides for a method of monitoring both bulk (total) microbiological activity and surface associated microbiological activity.

DETAILED DESCRIPTION OF THE INVENTION

Definitions of Terms

Figure 1:
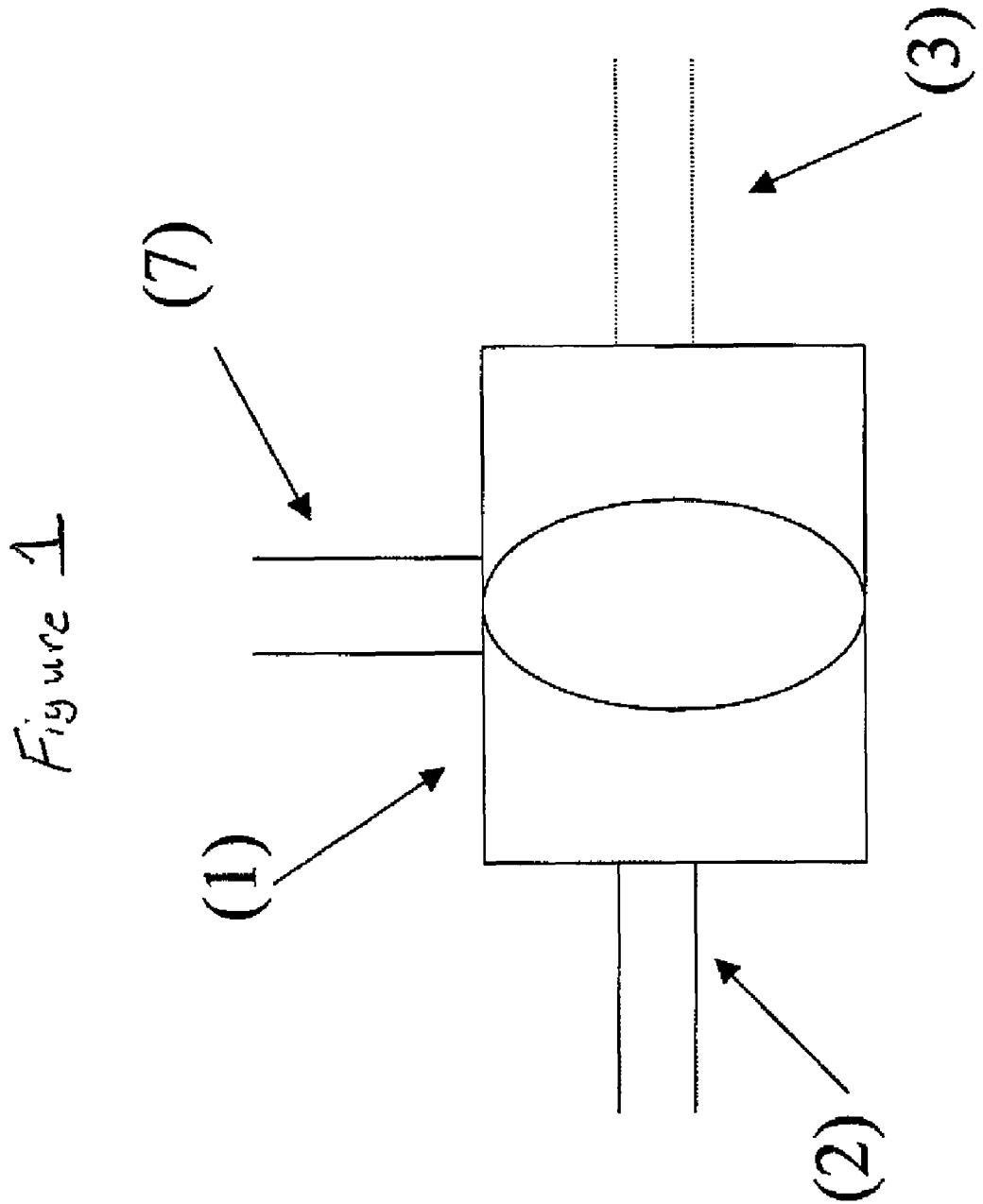
FIG. 1 shows a schematic of an apparatus containing a flow cell, a DO probe, a cleaning device, and optionally an ORP probe.

"DO" means dissolved oxygen.

"DO probe" includes any kind of probe that can measure dissolved oxygen. Preferably, the DO probe is a luminescent dissolved oxygen probe ("DO probe"). "LDO" means luminescent dissolved oxygen. LDO probes measure dissolved oxygen based on lifetime fluorescence decay where the presence of oxygen shortens the fluorescence lifetime of an excited fluorophore. The fluorophore is immobilized in a film at the sensor surface and the excitation is provided with a blue LED (light emitting diode). LDO probes are available from Hach Company, Loveland, Colo. The probes usually have a sensor head that takes the measurement.

"ORP" means oxidation-reduction potential. An ORP probe is available from Walchem Corporation, Holliston, Mass.

"REDOX" refers to oxidation-reduction state.

"OFM" means optical fouling monitor. Any suitable optical fouling for the particular process to be monitored may be utilized. This includes any general deposition monitor, such as a quartz crystal microbalance.

"Valve" refers to any device that regulates the flow of a fluid.

"Cleaning device" is any device(s) that are capable of cleaning a surface, e.g. a DO probe surface, and/or ORP probe surface.

"Process stream" includes any fluid in an industrial process, e.g. fluid taken from a conduit in a papermaking process, and fluid from a headbox in a papermaking process.

Preferred Embodiments

Microbial activity in process streams can be indirectly measured by monitoring the consumption of dissolved oxygen because dissolved oxygen consumption is directly related to the amount of ATP that a cell is producing under aerobic respiration conditions and the amount of ATP that a cell produces can be correlated with the level of microbial activity in said process streams. The methods described in this invention are not suitable for process streams with low levels of DO where aerobic respiration is not the primary pathway of energy generation in microbial cells.

DO measurements collected from a process stream should be converted to percent saturation using pressure, temperature, and salinity values of the process stream. This helps normalize the data based on process fluctuations in these parameters. Temperature correction is especially important, as the temperature of the process stream being analyzed will drop 1-10 degrees Celsius during stop-flow conditions, which occurs when fluid is no longer being drawn into a flow cell.

To enhance the integrity of the correlation between dissolved oxygen consumption and microbiological activity the REDOX state of the process fluid has to be oxidizing such that oxygen consumption is not a result of chemical oxidation processes. Factors such as pH will influence the REDOX state of the process waters. Under high pH conditions, for example process waters having a pH greater than 9.5, can cause the oxidation of organic materials in process fluids even at elevated REDOX conditions.

Therefore, preferably the ORP of the process stream should be measured in conjunction with the DO concentration to make sure that dissolved oxygen consumption is primarily related to microbiological activity and not to process stream chemistry.

A. Apparatus

An apparatus has been developed to practically measure dissolved oxygen in process streams. Other analytical devices may be associated with this apparatus, e.g. an ORP probe.

As shown in FIG. 1, the apparatus contains (1) a flow cell; (2) a DO probe; optionally an (3) ORP probe; and (7) a cleaning device.

The (1) flow cell has a plurality of openings. These openings serve to allow fluid to flow through the (1) flow cell. The size and shape of the openings may vary; in particular, the type of process stream should be taking into account.

Figure 3:
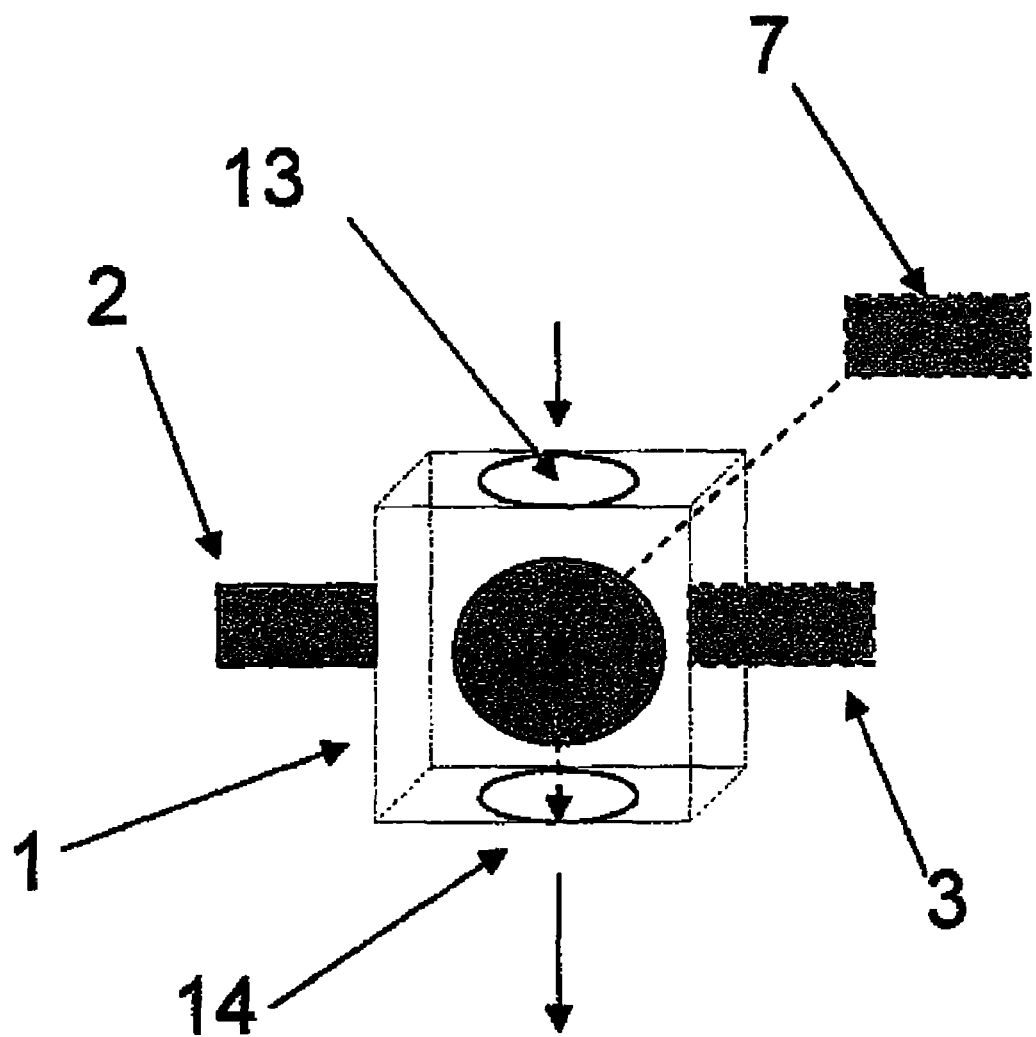
FIG. 3 shows a schematic of an apparatus containing a DO probe, an ORP probe, and a cleaning device.

FIG. 3 shows that (1) the flow cell contains (13) an inlet and (14) an outlet. The diameter of openings should be of a sufficient size to allow fluid from a process stream to flow easily through the (1) flow cell and prevent plugging of the (1) flow cell, and non-biological fouling of both the (2) DO probe and (3) ORP probe surfaces. Therefore, the diameter of the (1) flow cell will depend upon many factors, e.g. the type of process stream.

The flow cell openings also serve to allow various devices, such as (2) a DO probe, (3) an ORP probe, and/or (7) a cleaning device to attach to the flow cell so that one or more measurements of a process stream can be taken. Other apparatuses, such as pH meter, may associate with the flow cell.

In particular, the (2) DO probe and/or the (3) ORP probe are in communication with the (1) flow cell.

In one embodiment, the (2) DO probe and (3) ORP attach to the flow cell. The probes can attach to one of the (1) flow cell openings in various ways known to one of ordinary skill in the art. Connection can occur via any type of fastening and/or mounting means or the like. For example, a unit can be mounted to the (1) flow cell and a probe/device can be inserted through the unit and locked into place.

As shown in FIG. 3, the probes are flush to the wall of the (1) flow cell.

In one embodiment, at least a portion of said (2) DO probe and optionally an (3) ORP probe protrudes into said flow cell.

In another embodiment, (2) DO probe contains a DO sensor head, wherein at least a portion of said DO sensor head protrudes into said flow cell and optionally wherein said (3) ORP probe contains an ORP sensor head and wherein at least a portion of said ORP sensor head protrudes into said flow cell.

In another embodiment, the probes should be orientated in such a manner as not to significantly obstruct the flow of fluid through the (1) flow cell.

In another embodiment, the (2) DO probe and (3) ORP probe are positioned across from one another.

Figure 2:
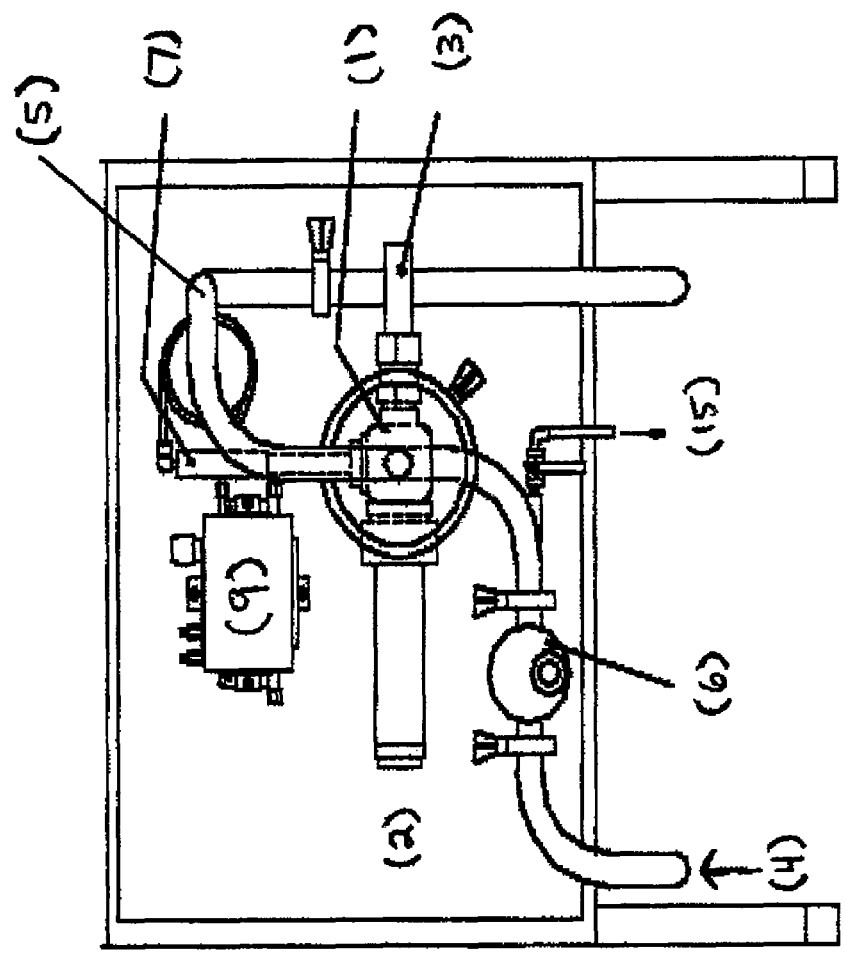
FIG. 2 shows schematic of an apparatus mounted to a back plate within an enclosure, wherein the apparatus contains a flow cell, a DO probe, an ORP probe, a cleaning device with a wiper solenoid, a first conduit, a second conduit, and a valve.

FIG. 2 shows additional features of the apparatus. More specifically, FIG. 2 shows (4) a first conduit, (6) a valve associated with (4) a first conduit, (15) a drain associated with (4) a first conduit, (1) a flow cell, (2) a DO probe, (3) an ORP probe, (7) a cleaning device, (9) a solenoid in communication with said (7) cleaning device, and (S) a second conduit.

The (4) first conduit and a (5) second conduit attach to one or more openings in said (1) flow cell, as well as to the housing of the process stream. Attachment can occur via various means known to those of ordinary skill in the art. For example, the (4) first conduit can be piped into the process stream.

The (4) first conduit serves to carry fluid and/or divert fluid from the process stream into the (1) flow cell and/or other apparatuses such as an OFM. The (4) first conduit may be situated in any way that facilitates the movement of fluid from the process stream to the (1) flow cell. For example, gravity or an energy-based mechanism such as a pump can draw fluid from the process stream into the (1) flow cell containing apparatus.

In another embodiment, a drain (15) may be associated with the (4) first conduit to prevent backup/restrict flow into the process stream.

The (5) second conduit serves as exit path for fluid flowing through (1) a flow cell and also as a reservoir for holding fluid from a process stream. In particular, the second conduit (5) may be spatially orientated so that the (1) flow cell maintains fluid inside the (1) flow cell for analysis when monitoring is under stop flow conditions. For example, the (5) second conduit is orientated so that gravity can hold fluid inside the (1) flow cell.

In another embodiment, the (5) second conduit may also act as a drain.

The (6) valve associates with the (1) flow cell. In particular, the (6) valve is in communication with the (1) flow cell in a manner to achieve its desired function. The (6) valve(s) control/regulate the flow of fluid from the process stream into the (1) flow cell.

In one embodiment, the (6) valve associates with the flow cell via the (4) first conduit. In particular, the (6) valve integrates/connects with the (4) first conduit in such a manner as to be able to restrict flow in the closed position and allow flow when the (6) valve is under open conditions.

In another embodiment, (6) a valve(s) may regulate the flow of fluid into an OFM and/or the (1) flow cell.

In another embodiment, the diameter of the (6) valve must be large enough so as not to impede the flow of process water that contains high solids.

In another embodiment, (6) a valve may also prevent fluid from exiting the (1) flow cell or (5) second conduit so that readings under closed flow conditions can occur.

In another embodiment, the diameter of the (6) valve is at least 1 inch.

In another embodiment, the (6) valve is a ball valve.

In another embodiment, the (6) valve is actuated manually, electrically or pneumatically.

In another embodiment, the ball (6) valve is actuated manually, electrically or pneumatically.

Figure 4:
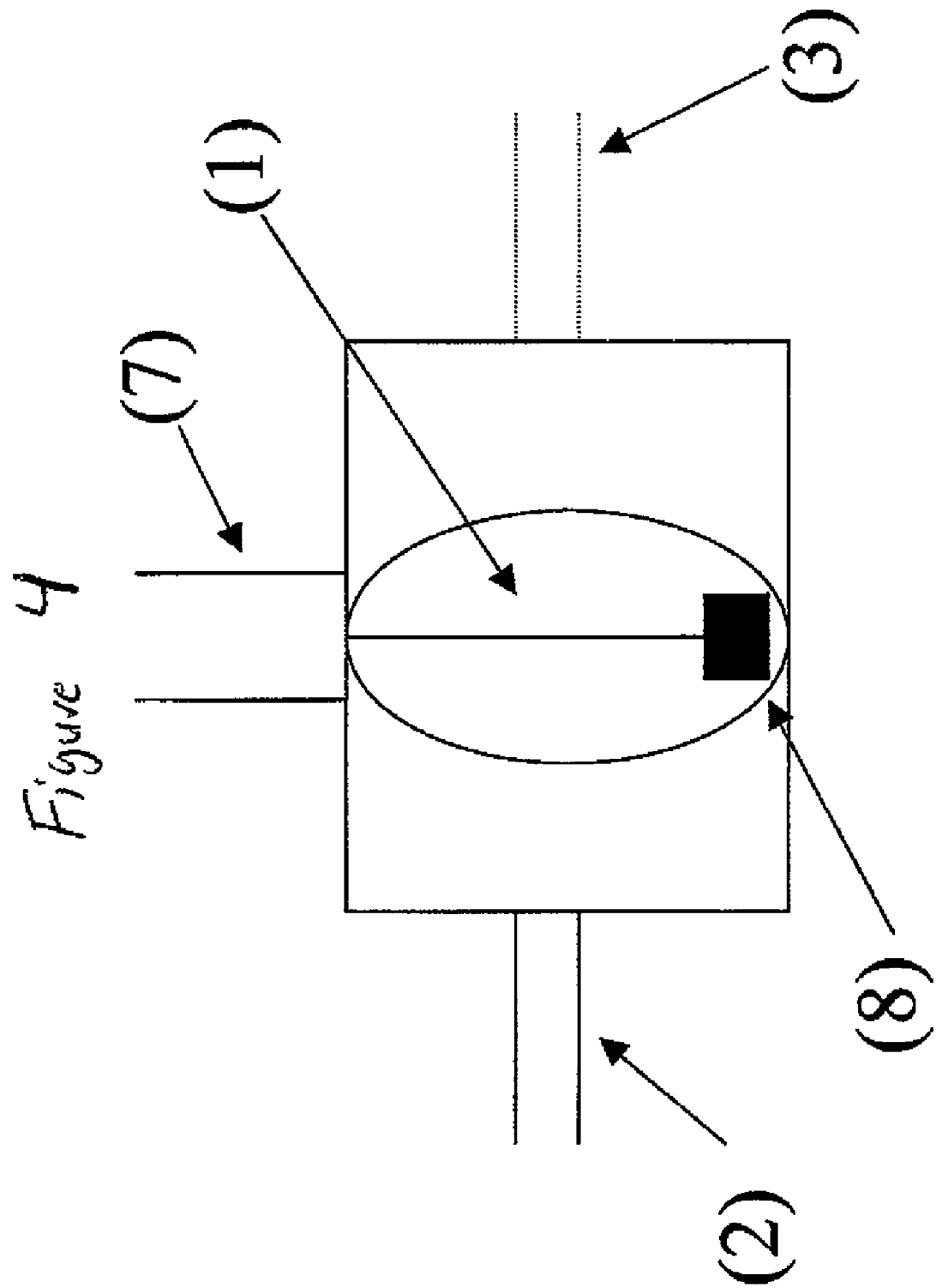
FIG. 4 shows a schematic of an apparatus containing a flow cell, an ORP probe, a DO probe, and a cleaning device containing a wiper blade.

FIGS. 2 and 4 show that a (7) cleaning device may be attached to one of the (1) flow cell openings. The cleaning device serves to clean the surface of both the (2) DO probe and/or (3) ORP probe surfaces and the orientation of the device should be such to achieve this function. The (7) cleaning device may clean other devices associated with the (1) flow cell.

In one embodiment, the (7) cleaning device traverses the area of the (1) flow cell.

In another embodiment, the (7) cleaning device is capable of traversing the area of the (1) flow cell to clean one or more devices/probes, such (2) a DO probe, (3) an ORP probe, or other types of analytical instrumentation that may be associated with the (1) flow cell.

In another embodiment, the (7) cleaning device contains (8) a wiper blade or a brush.

In another embodiment, the (7) cleaning device is actuated by a (9) wiper solenoid. The (9) solenoid receives instructions from a controller that is programmed with logic that instructs when to clean and when not to clean.

As shown in FIG. 4, a (8) wiper blade is positioned to traverse the (1) flow cell in a perpendicular direction relative to both the (2) DO probe and (3) ORP probe.

Figure 5:
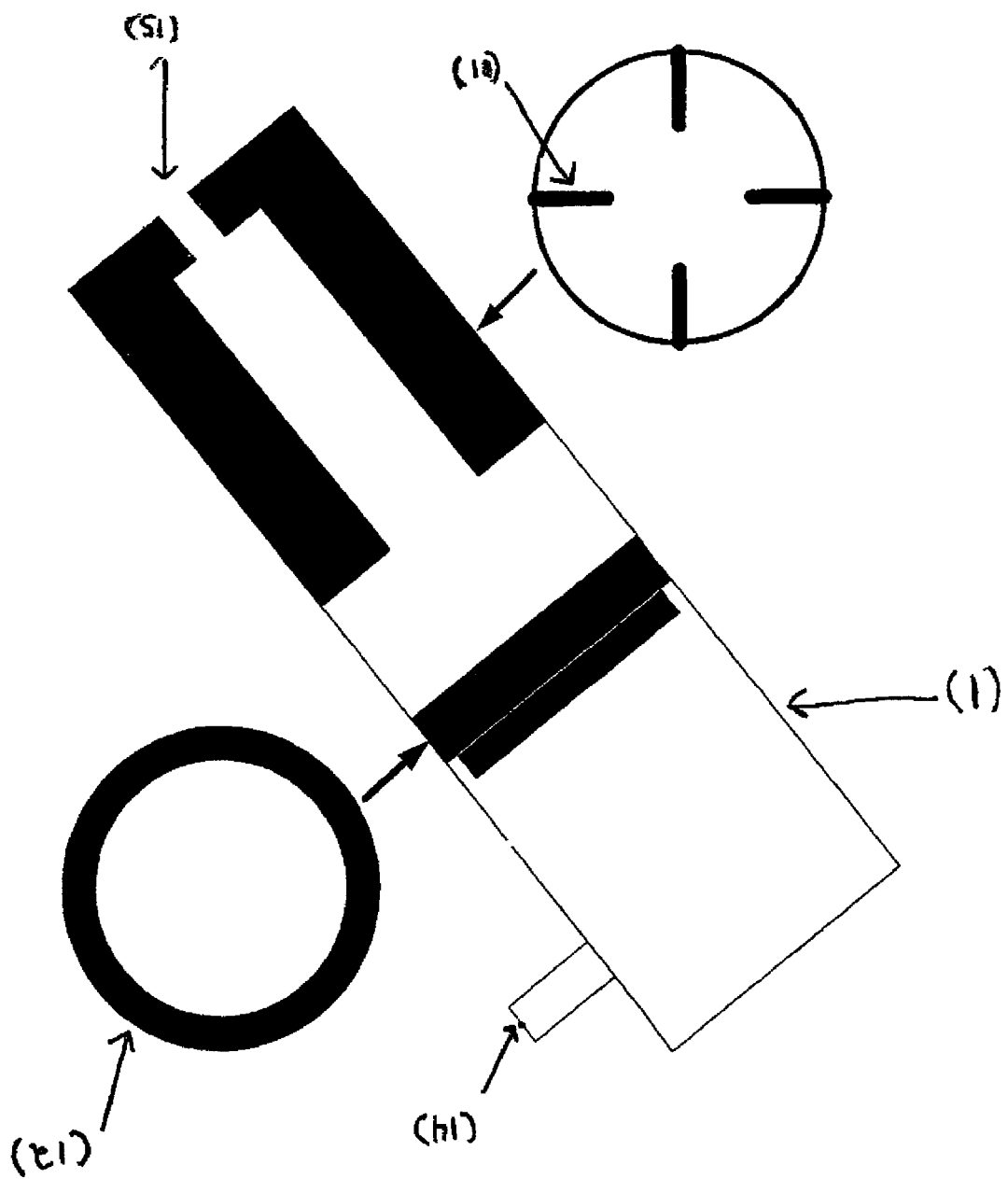
FIG. 5 shows a schematic of a flow cell and a member, used to increase surface area

Adding one or more (11) baffles to the (1) flow cell can increase the area of the (1) flow cell. FIG. 5 shows a modified flow cell. Specifically, the member attaches to the flow cell and the member contains more than one baffle. The member can attach to the flow cell in a variety of ways. Other objects that can increase the surface area may be utilized in a similar fashion.

In one embodiment, the (10) member secures onto the (1) flow cell with the assistance of an (12) adaptor. The member has a (15) member inlet that receives flow from said process stream and an outlet that attaches to the flow cell.

In one embodiment, the (4) first conduit attaches to the (10) member instead of directly to the (1) flow cell.

In another embodiment, the (10) member has one or more (11) baffles.

The apparatus may be configured to monitor bulk microbiological water activity, surface-associated microbiological activity, or a combination thereof.

B. Monitoring Bulk Microbiological Activity in a Process Stream

A method of monitoring bulk (total) microbiological activity in a process stream is disclosed. Bulk (total) microbiological activity refers to microbial activity in the bulk process stream, such as planktonic microorganisms and sessile microorganisms in the process stream.

The bulk microbiological activity of a process stream is determined by measuring the DO concentration of the process stream. Other parameters may be utilized in conjunction with this analysis. More specifically, the methodology contains the following steps: (a) connecting an apparatus to a process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally an ORP probe attached to one of said openings, optionally a cleaning device attached to one of said openings, optionally a first conduit attached to the flow cell inlet, optionally a second conduit attached to the flow cell outlet, and optionally a valve associated with said flow cell; (b) drawing fluid from said process steam into said flow cell; (c) opening the valve of said apparatus to allow fluid to be drawn into said flow cell; (d) measuring at least once the DO concentration of said process stream with said DO probe, and wherein prior to each measurement the surface of said DO probe is cleaned; (e) closing the valve of said apparatus to prevent fluid from being drawn into said flow cell; (f) measuring at least once the DO concentration of the fluid inside said apparatus with said DO probe and wherein prior to each measurement the surface of said DO probe is cleaned; (g) calculating a $\Delta$ DO reading between step (d) and step (f); and h) correlating at least said $\Delta$ DO value in step (g) with bulk (total) microbiological activity in said process stream.

This methodology may be applied to various different types of process streams.

In one embodiment, the process stream is from a process selected from the group consisting of: a paper making process; a cooling water process; a food or beverage process; and recreational based process.

Bulk water microbiological activity is measured by looking at the change in DO concentration ($\Delta$ DO) between open-flow and stop-flow conditions. Other parameters may be utilized in conjunction with this analysis. More specifically, by looking at the $\Delta$ DO, the consumption rate of the DO can be determined. The consumption rate of DO can then be correlated with microbiological activity in said process stream, but the integrity of the correlation is better when ORP is measured in conjunction with the DO measurement because the DO measurement may be affected when the REDOX state of the process stream fluid is not oxidizing.

Open-flow conditions occur when the process stream fluid can pass through flow cell and be measured by analytical instrumentation that is in communication with the flow cell, particularly a DO probe for measuring the DO concentration of the fluid.

Stop-flow conditions refer to when a process stream fluid can no longer enter the flow cell. Under stop-flow conditions, fluid is maintained in the flow cell and the flow cell monitors the DO concentration of that fluid.

Under open flow conditions, such is in step (d), the DO concentration of the process stream fluid should be measured for a sufficient amount of time so that an accurate reading of the DO concentration of the process stream can be obtained. This may take one reading or more. One of ordinary skill in the art would be able to determine without undue experimentation the number of readings it would take to get an accurate process stream reading, as well as the interval of reading(s) it would take to get an accurate process stream reading.

Under stop-flow conditions, such as in step (f, a sufficient amount of time should lapse prior to the first DO measurement of the fluid in the flow cell to ensure that one or more microbiological species in said fluid will have enough time to consume dissolved oxygen in said fluid. This time period may vary and depends upon one or more factors, which may include the type of process that is being monitored and the effectiveness of the microbiological program, which is being used prior to implementing the methodologies of the present invention. For example, in the paper industry, if the process water is heavily contaminated with microorganisms it may take less time for microorganisms to consume the DO. The types of microorganisms (e.g. fungi or filamentous bacteria) might also impact the rate and extent of DO consumption.

In one embodiment, measurements taken under open flow conditions and stop flow conditions are taken at the same intervals of time. In a further embodiment, measurements taken under open flow conditions and stop flow conditions are taken for the same time period and at the same intervals of time.

The process stream may be monitored continuously, intermittently, or one time. Continuous monitoring provides real-time conditions so that system upsets can be readily detected in the process stream.

The $\Delta$ DO may be calculated in various ways.

In one embodiment, bulk microbiological activity is measured by taking the maximum change in DO concentration during a period of continuous water flow (open-flow conditions) versus stop flow conditions when the process water is stopped by closing the valve. In other words, the maximum change in DO concentration based upon readings in step (d) and step (f) are used to calculate the $\Delta$ DO.

In another embodiment, the $\Delta$ DO value is determined by taking the average DO measurement from step (d) and the minimum DO level from step (f).

In another embodiment, the $\Delta$ DO value is determined by taking the highest measurement from step (d) and the minimum DO level from step (f).

In another embodiment, the $\Delta$ DO value is determined by taking the last measurement from step (d) and the minimum DO level from step (f).

In another embodiment, the duration of measurement and the interval of measurement for step (d) and step (f) are the same.

In a further embodiment, the duration of measurement in step (d) and step (f) can be anywhere from 5 to 240 minutes.

In yet a further embodiment, the duration is 30 minutes and measurements are recorded 5 times during step (d) and step (f) at equal intervals.

In yet a further embodiment, the surface is wiped clean followed by a 30 second delay before measurements are recorded in step (d) and step (f).

The ORP of the process stream may be measured in conjunction with DO concentration of the process stream.

In one embodiment, the method further comprises measuring ORP in step (d) and step (f) at least one time and prior to each measurement cleaning the ORP probe surface.

In another embodiment, one or more oxidants may be added to the process stream if the ORP value drops below a predetermined level, In another embodiment, if the ORP measurement(s) drops below a predetermined level, then the DO measurements that are measured in conjunction with the ORP measurements are not included in calculating Δ DO. More specifically, by excluding these measurements, a process operator can get a better feel as to whether the DO consumption is related to microbiological activity or process stream chemistry.

In another embodiment, if the predetermined level is less than about 100 mV, then DO measurements are excluded because when ORP is in this range, the conditions are typically not oxidizing and consumption of dissolved oxygen could be related to chemical conditions in the process stream.

Responding to total (bulk) microbiological levels in a process stream can take many different routes.

In one embodiment, if the total (bulk) microbiological levels are high or above a predetermined level thought to work well for the process, the protocol involves adding an effective amount of biocide to bring microbiological levels back to a desired level.

The biocides can be oxidizing and/or non-oxidizing.

With respect to a papermaking process, the biocides are selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; Stabrex™ (bromosulfamate); bromo-chloro-dimethyl hydantoin; dichlorodimethyl hydantoin; monochloramine; sodium hypochlorite used in combination with ammonium salts and stabilizers including dimethyl hydantoin, amino acids, cyanuric acid, succinimide, and urea; and a combination thereof.

One or more controllers may be used to implement a response to the level of microbiological activity in the process stream. More specifically, the controllers can be programmed to receive data from the process stream, e.g. the DO probe, calculate a Δ DO based upon logic inputted into the controller (e.g. a program logic controller), and implement a response in accord with the Δ DO, which could include various actions such as actuating a pump that feeds biocide or deposit control polymers into a process stream.

In one embodiment, the controller is web-based.

In another embodiment, the controller may be in communication with at least one of the following: the ORP probe, the DO probe, the cleaning device, a valve, or a combination thereof.

In another embodiment, the controller receives input signals from said DO probe, and implements a desired protocol that is programmed in said controller.

In another embodiment, the controller is a controller system. "Controller system" and similar terms refer to a manual operator or an electronic device having components such as a processor, memory device, cathode ray tube, liquid crystal display, plasma display, touch screen, or other monitor, and/or other components. In certain instances, the controller may be operable for integration with one or more application-specific integrated circuits, programs, or algorithms, one or more hard-wired devices, and/or one or more mechanical devices. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms.

In another embodiment, the desired protocol will be alerting an operator or person in charge of monitoring the process stream and treating the process stream.

In another embodiment, the desired protocol involves the addition of an effective amount of biocide to the process stream if said Δ DO reaches a predetermined level. The biocide can be oxidizing and/or non-oxidizing.

An optical fouling monitor (OFM) may be used in conjunction with said flow cell to determine the nature/origin of the deposit buildup that is occurring in the process stream.

In one embodiment, the methodology of the present invention further comprises providing an optical fouling monitor that is in communication with said process stream; drawing fluid from said process stream into said optical fouling monitor; measuring deposit formation with the optical fouling monitor; determining the type of deposits by correlating deposit formation in the optical fouling monitor with said microbiological activity determined from the Δ DO in said process stream; optionally programming a controller that is in communication with said OFM and at least the DO probe to add one or more chemical species to said process stream in response to the correlation between said deposit formation and microbiological activity.

In a further embodiment, the chemical species contains a biocide if said correlation indicates that deposits formed on the optical fouling are microbiological in nature. For example, if there is deposition on the OFM and the Δ DO is high, then adding biocide to said process stream to combat deposit formation and lower the microbiological activity of the process stream is one course of action. The biocides can be oxidizing and/or non-oxidizing.

In yet a further embodiment, the chemical species is a deposit control chemistry if said correlation indicates that said deposition formation is not microbiological in nature. For example, if there is deposition on the OFM and the Δ DO is low, then adding deposit control chemistry to the process stream to combat deposit formation is one course of action. There are various types of deposit control chemistries that are known to one of ordinary skill in the art; for example, there are anti-pitch agents that assist in preventing deposit formation during a papermaking process, and deposit control polymers.

C. Monitoring Surface-Associated Microbiological Activity in a Process Stream Surface-associated microbiological activity refers to microbial activity of surface microorganisms, for example, biofilms.

The surface-associated microbiological activity of a process stream is determined by measuring the DO concentration of the process stream. Other parameters may be utilized in conjunction with this analysis. More specifically, the methodology contains the following steps: (a) connecting an apparatus to a process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally an ORP probe attached to one of said openings, optionally a cleaning device attached to one of said openings, optionally a first conduit attached to the flow cell inlet, optionally a second conduit attached to the flow cell outlet, and optionally a valve associated with said flow cell; (b) drawing fluid from said process steam into said flow cell; (c) opening the valve of said apparatus to allow fluid to be drawn into said flow cell; (d) measuring at least once the DO concentration of said process stream with said DO probe, and wherein said DO probe is not cleaned prior to each measurement; (e) cleaning the surface of said DO probe; (f) measuring at least once the DO concentration of the fluid inside said apparatus with said DO probe and optionally wherein prior to each measurement said DO probe surface is cleaned; (g) calculating a $\Delta$ DO reading between step (d) and step (f); and (h) correlating at least said $\Delta$ DO in step (g) with surface associated biological activity.

This methodology may be applied to various different types of process streams.

In one embodiment, the process stream is from a process selected from the group consisting of: a paper making process; a cooling water process; a food or beverage process; and recreational based process.

Biofilm activity is calculated by the difference in DO measurements taken before wiping versus immediately after wiping during open-flow conditions. Other parameters may be utilized in conjunction with this analysis. The integrity of the correlation of the $\Delta$ DO with biofilm activity is better when ORP is measured in conjunction with the DO measurement because the DO measurement may be affected when the REDOX state of the process stream fluid is not oxidizing.

Open-flow conditions occur when the process stream fluid can pass through the flow cell and be measured by analytical instrumentation that is communication with the flow cell, particularly a DO probe for measuring the DO concentration of the fluid.

Under open-flow conditions, such as in step (d) and step (f), a sufficient amount of time prior to measuring DO should lapse so that if there is biofilm accumulation, then there will be a sufficient amount of time for biofilm accumulation to occur. This time period may vary on various factors including the type of process being monitored and the effectiveness of the current microbiological program, which is currently being used prior to implementation of this methodology. For example, in the paper industry, if the process water is heavily contaminated with microorganisms it may take less time for microorganisms to consume the DO. The types of microorganisms (e.g. fungi or filamentous bacteria) might also impact the rate and extent of DO consumption.

In one embodiment, measurements taken under open flow conditions and stop flow conditions are taken at the same intervals of time. In a further embodiment, measurements taken under open flow conditions and stop flow conditions are taken for the same time period and at the same intervals of time.

The process stream may be monitored continuously, intermittently, or one time. Continuous monitoring provides real-time conditions so that system upsets can be readily detected in the process stream.

The $\Delta$ DO may be calculated in various ways.

In one embodiment, the $\Delta$ DO value is determined by taking the lowest DO measurement in step (d) and average DO measurement from step (f).

In another embodiment, the $\Delta$ DO value is determined by taking the lowest measurement from step (d) and the highest DO level from step (f).

In another embodiment, the $\Delta$ DO value is determined by taking the last measurement from step (d) and the highest DO level from step (f).

In another embodiment, the DO measurements are made and recorded 5 times during a selected time interval with the flow continuous but there is no probe cleaning with wiper blade prior to any of these measurements.

In another embodiment, one minute before the selected time interval expires, the probes are cleaned and two consecutive measurements made and recorded.

The ORP of the process stream may be measured in conjunction with DO concentration of the process stream.

In one embodiment, the method further comprises measuring ORP in step (d) and step (f) at least one time and prior to each measurement cleaning the ORP probe surface, wherein the ORP probe is not wiped clean in step (d) and optionally wherein said ORP probe is wiped clean in step (f). Optionally, one or more oxidants may be added to the process stream if the ORP value drops below a predetermined level.

In another embodiment, if said ORP measurements drop below a predetermined level, then the DO measurements that are measured in conjunction with the ORP measurements, may not be included in calculating $\Delta$ DO which is used in determining microbiological activity of the process stream. More specifically, by excluding these measurements, a process operator can get a better feel as to whether the DO consumption is related to microbiological activity or process stream chemistry.

In another embodiment, if the predetermined level is less than about 100 mV, then DO measurements are excluded because when ORP is in this range, the conditions are not oxidizing and consumption of dissolved oxygen could be related to chemical conditions in the process stream.

In another embodiment, the DO probe, the ORP probe, or a combination thereof are cleaned by a cleaning device that contains a wiper blade.

In another embodiment, the wiper blade wipes the probe(s) surface twice.

Responding to surface-associated microbiological levels in a process stream can take many different routes.

In one embodiment, if the surface associated microbiological levels are high or above a predetermined level thought to work well for the process, the protocol involves adding an effective amount of biocide to bring microbiological levels back to a desired level.

The biocides can be oxidizing and/or non-oxidizing.

With respect to a papermaking process, the biocides are selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; Stabrex™ (bromosulfamate); bromo-chloro-dimethyl hydantoin; dichloro-dimethyl hydantoin; monochloramine; sodium hypochlorite used in combination with ammonium salts and stabilizers including dimethyl hydantoin, amino acids, cyanuric acid, succinimide, and urea; and a combination thereof.

One or more controllers may be used to implement a response to the level of microbiological activity in the process stream. More specifically, the controllers can be programmed to receive data from the process stream, e.g. the DO probe, calculate a $\Delta$ DO based upon logic inputted into the controller (e.g. a program logic controller), and implement a response in accord with the Δ DO, which could include various actions such as actuating a pump that feeds biocide into a process stream.

In one embodiment, the controller is web-based.

In another embodiment, the controller may be in communication with at least one of the following: the ORP probe, the DO probe, the cleaning device, a valve, or a combination thereof.

In another embodiment, the controller receives input signals from said DO probe, and implements a desired protocol that is programmed in said controller.

In another embodiment, the controller is a controller system. "Controller system" and similar terms refer to a manual operator or an electronic device having components such as a processor, memory device, cathode ray tube, liquid crystal display, plasma display, touch screen, or other monitor, and/or other components. In certain instances, the controller may be operable for integration with one or more application-specific integrated circuits, programs, or algorithms, one or more hard-wired devices, and/or one or more mechanical devices. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms.

In another embodiment, the desired protocol will be alerting an operator or person in charge of monitoring the process stream and treating the process stream.

In another embodiment, the desired protocol involves the addition of an effective amount of biocide to the process stream if said Δ DO reaches a predetermined level. The biocide can be oxidizing and/or non-oxidizing.

An optical fouling monitor (OFM) may be used in conjunction with said flow cell to determine the nature/origin of the deposit buildup that is occurring in the process stream.

In one embodiment, the methodology of the present invention further comprises providing an optical fouling monitor that is in communication with said process stream; drawing fluid from said process stream into said optical fouling monitor; measuring deposit formation with the optical fouling monitor; determining the type of deposits by correlating deposit formation in the optical fouling monitor with said microbiological activity determined from the Δ DO in said process stream; optionally programming a controller that is in communication with said OFM and at least the DO probe to add one or more chemical species to said process stream in response to the correlation between said deposit formation and microbiological activity.

In a further embodiment, the chemical species contains a biocide if said correlation indicates that deposits formed on the optical fouling are microbiological in nature. For example, if there is deposition on the OFM and the Δ DO is high, then adding biocide to said process stream to combat deposit formation and lower the microbiological activity of the process stream is one course of action. The biocide can be oxidizing and/or non-oxidizing.

In yet a further embodiment, the chemical species is a deposit control chemistry if said correlation indicates that said deposition formation is not microbiological in nature. For example, if there is deposition on the OFM and the Δ DO is low, then adding deposit control chemistry to the process stream to combat deposit formation is one course of action. There are various types of deposit control chemistries that are known to one of ordinary skill in the art; for example, there are anti-pitch agents that assist in preventing deposit formation during a papermaking process, and deposit control polymers.

D. Monitoring Bulk and Surface Associated Microbiological Activity in a Process Stream Bulk microbiological activity may be monitored in conjunction with surface associated microbiological activity. A method of measuring bulk microbiological activity and surface associated microbiological activity in a process stream comprising: (a) connecting an apparatus to said process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally. an ORP probe attached to one of said openings, optionally a cleaning device attached to one of said openings, optionally a first conduit attached to the flow cell inlet, optionally a second conduit attached to the flow cell outlet, and optionally a valve associated with said flow cell; (b) drawing fluid from said process steam into said flow cell; (c) opening the valve of said apparatus to allow fluid to be drawn into said flow cell; (d) measuring at least once both the DO concentration of said process stream with said DO probe, wherein said DO probe is not cleaned prior to each measurement; (e) cleaning the surface of said DO probe; (f) measuring at least once the DO concentration of the fluid inside said apparatus with said DO probe optionally wherein prior to each measurement said DO probe surface is cleaned; (g) closing the valve of said apparatus to prevent fluid from being drawn into said flow cell; (h) measuring at least once the DO concentration of the fluid inside said apparatus with said DO probe, wherein prior to each measurement said DO probe surface is cleaned; (i) calculating a Δ DO reading between step (f) and step (h) and correlating at least said Δ DO with said bulk microbiological activity in said process stream; and (j) calculating a Δ DO reading between step (d) and step (f) and correlating at least said Δ DO with said surface associated microbiological activity in said process stream.

Figure 8:
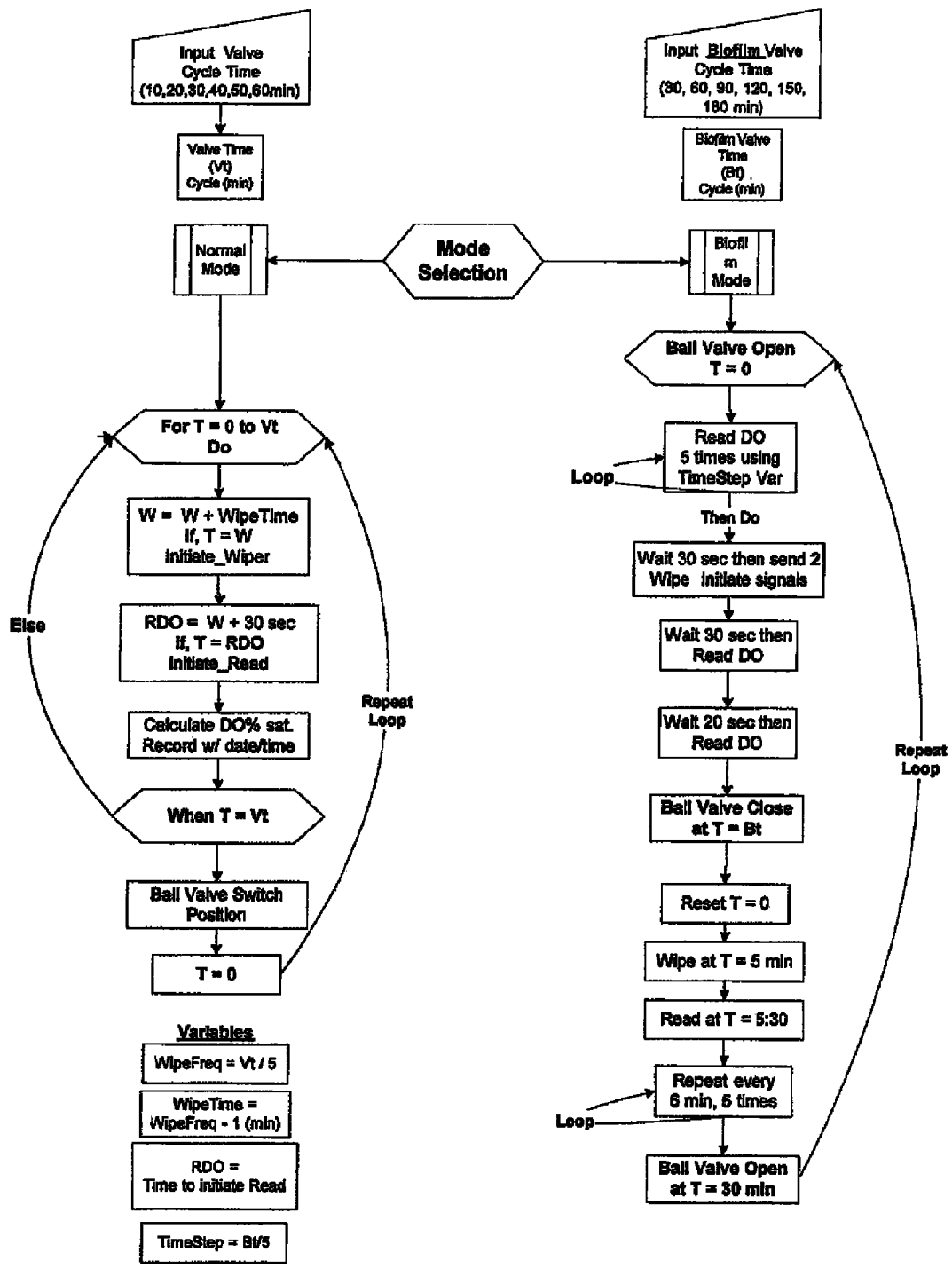
FIG. 8 shows a flow chart for monitoring bulk microbiological activity and/or surface associated microbiological activity.

In another embodiment, the monitoring is set up so that an operator can toggle/switch between bulk microbiological activity (Normal Mode) and/or surface associated activity (Biofilm Mode). FIG. 8 illustrates one embodiment of this mechanism via a flow chart.

In another embodiment, the method further comprises measuring ORP in step (d), step (f), and step (h) at least one time, wherein the ORP probe is not wiped clean in step (d), optionally wherein said ORP probe is wiped clean in step (f), and wherein the ORP probe is wiped clean in step (h); optionally adding one or more oxidants to said process stream if the ORP value drops below a predetermined level; and optionally not using said DO measurements in calculating said Δ DO if said ORP value drops below a predetermined level.

In another embodiment, deposit formation from the process stream may be also monitored in conjunction with this methodology. More specifically, the methodology of the present invention further comprises providing an optical fouling monitor that is in communication with said process stream; drawing fluid from said process stream into said optical fouling monitor; measuring deposit formation with said optical fouling monitor; determining the type of deposits by correlating deposit formation in said optical fouling monitor with said microbiological activity determined from the Δ DO in said process stream; optionally programming a controller to add one or more chemical species to said process stream in response to said correlation between said deposition formation and microbiological activity.

The following examples are at not meant to be limiting.

EXAMPLES

Example 1

A process stream is drawn into a flow cell via a first conduit. One or more valves regulate flow into a flow cell. A drain associated with the first conduit and one or more valves prevents backup into the process stream or aids in controlling plugging from solids present in the process stream. Under open flow conditions the valve is positioned to allow fluid to pass into the flow cell. Attached to the flow cell are a DO probe, an ORP probe, and a cleaning device (e.g. wiper blade). Fluid passes through the flow cell for analysis.

Figure 9:
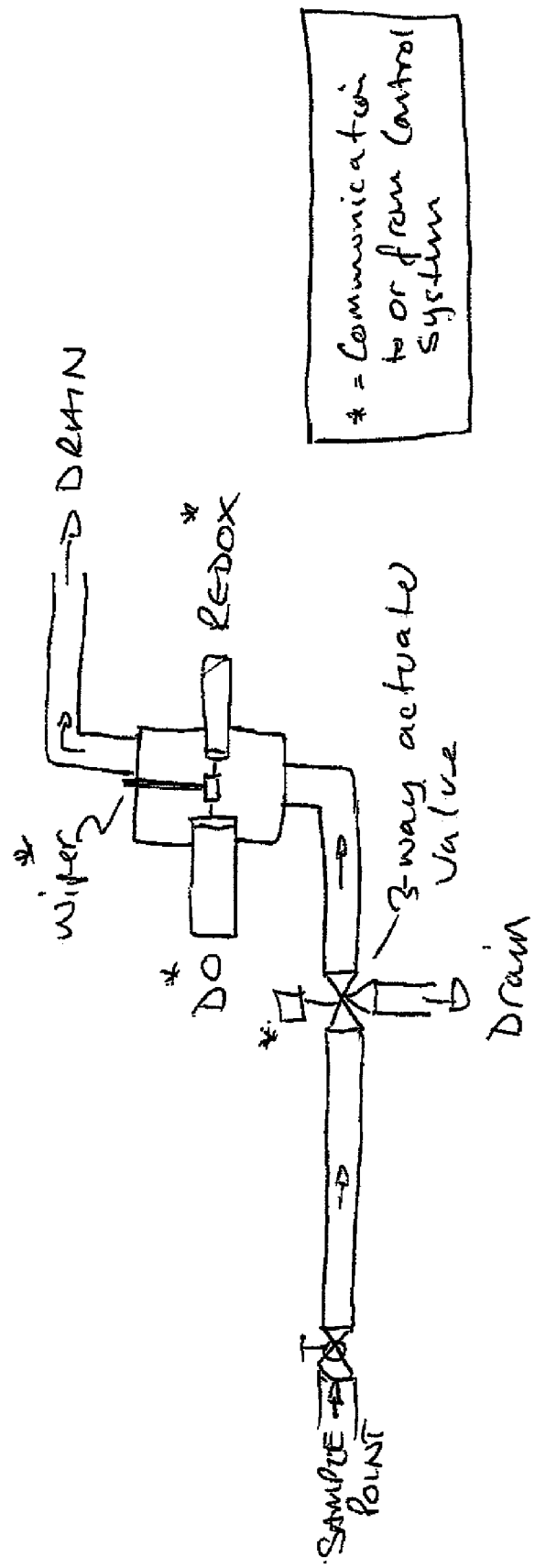
FIG. 9 illustrates one embodiment of the claimed invention, wherein there is a flow cell associated with a DO probe, an ORP probe, and a cleaning device.

Depending on the monitoring (bulk/surface-associated/a combination), the valve is turned in an open position/or closed position to allow fluid into the flow cell and the DO concentration and/or ORP is recorded in accord with one of the above-mentioned process protocols. The fluid that passes through the flow cell exits through a drain. The fluid that flows into the drain can be drained back into the process stream, e.g. into the machine chest of a papermaking process. FIG. 9 provides a schematic of the flow cell setup and the flow of a process stream through the flow cell setup.

Figure 10:
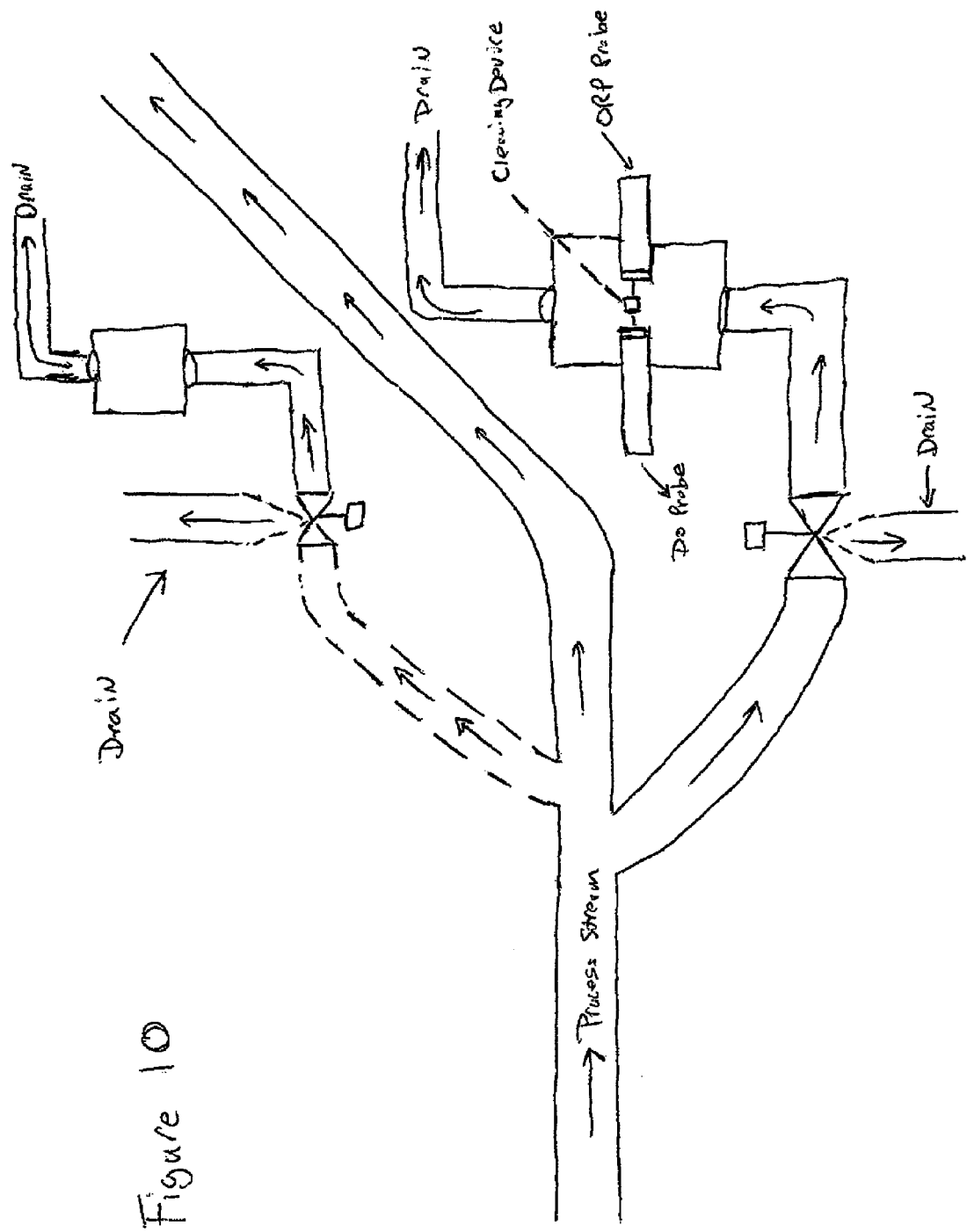
FIG. 10 illustrates one embodiment of the claimed invention, wherein there is an OFM and a flow cell associated with a DO probe, an ORP probe, and a cleaning device.

An OFM monitor can also be associated with the process stream. One or more valves regulate flow into an OFM. FIG. 10 provides a schematic of the flow cell setup in conjunction with an OFM monitor, as well as the flow of the process stream through the flow cell setup and OFM.

Depending upon the level of microbiological activity and/or deposits in the process stream, the appropriate chemistry that corrects the problem can be feed into the process stream. For example, a controller may transmit a signal a pump that actuates a solenoid associated with a feed mechanism.

Example 2

A side-stream of paper process water from a paper mill located in Germany was allowed to flow through the monitoring device (2 liters per second). This mill produces coated and uncoated freesheet and uses a stabilized-oxidant for biocontrol. The valve on the monitoring device was opened and closed at 60-minute intervals to start and stop flow into the flow-cell monitoring chamber. ORP and LDO values were measured at 10-minute intervals. Data from the ORP and LDO monitoring devices were collected by a data logger and sent to a web-server for display on a website. Data were downloaded from the website and analyzed to determine the impact of the biocontrol program and process conditions on microbial activity.

Figure 6:
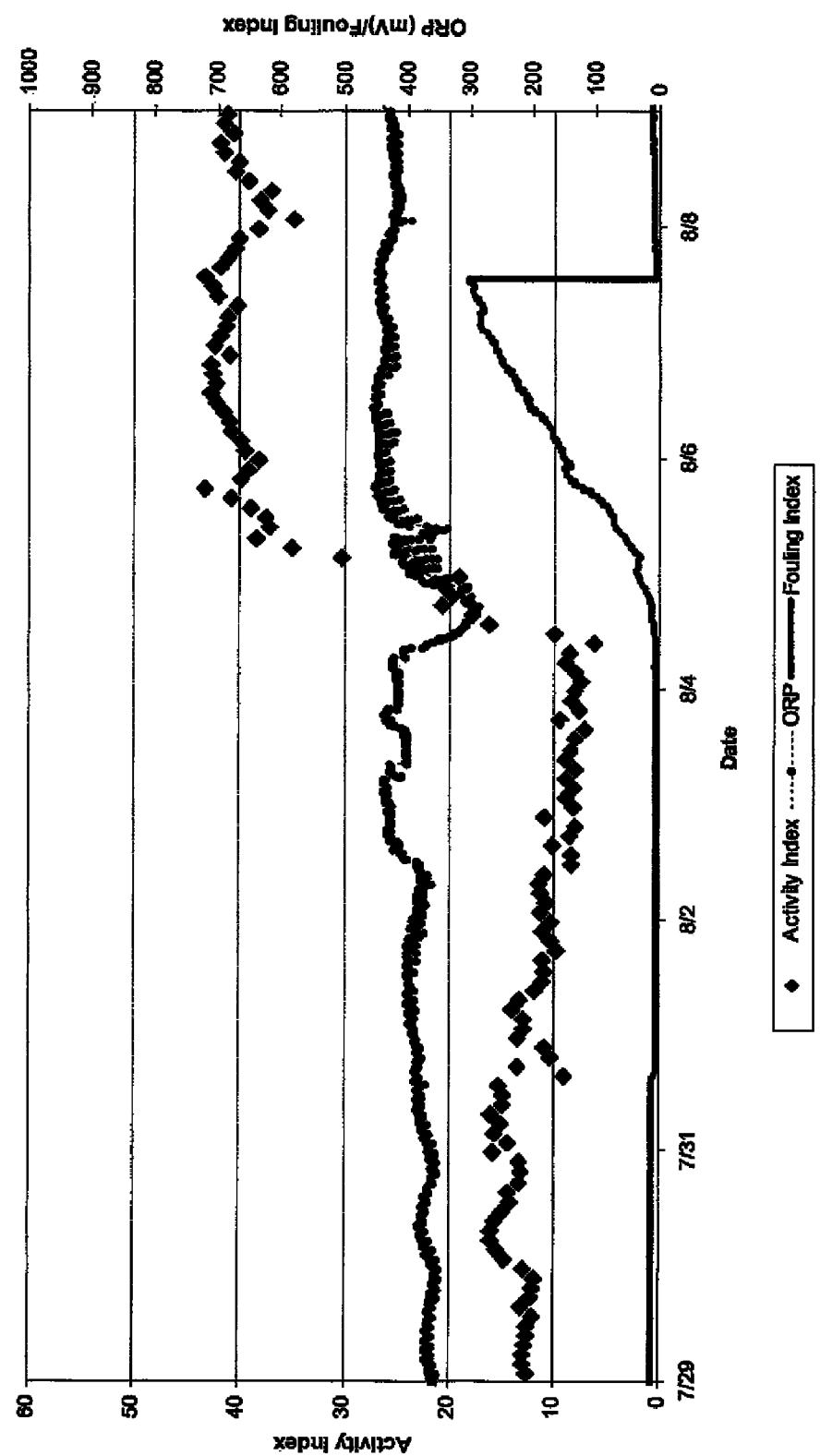
FIG. 6 shows data collected at a paper mill, which pertains to bulk (total) microbiological activity and surface-fouling.

In this application, the invention was used in combination with an OFM to determine the nature/origin of problematic deposits. For example, if deposition and activity are high it is likely that deposits are biological in nature. In contrast, if deposition is high and microbial activity is low it is unlikely that microorganisms are contributing to deposits and problem-solving efforts should be focused elsewhere. The example provided in FIG. 6 demonstrates the impact of a machine shut-down on ORP, microbial activity, and deposition (OFM) in stagnant process water. Microbial activity is reported as Δ DO. The machine was shut-down on August 4. Shortly following this event there was a sharp increase in the Δ DO, which coincided with a decrease in ORP and increase in surface fouling as measured by the OFM. These data suggest that the oxidant-based program was not persistent and did not adequately control microbial growth and deposit formation during this incident. Microscopic examination of surface deposits confirmed high densities of microorganisms, including filamentous bacteria.

Example 3

A side-stream of paper process water from a paper mill located in the U.S. was allowed to flow through the monitoring device (0.25 liters per second). This mill frequently changes the fiber content of the paper product, which can have a dramatic impact on the performance of a biocontrol program. Specifically, this mill uses an Azoto furnish that increases the halogen-demand in the process water system. The valve of the monitoring device was opened and closed at 30-minute intervals to start and stop flow into the flow-cell monitoring chamber. ORP and LDO values were measured at 6-minute intervals. The data from the ORP and LDO monitoring devices were collected by a data logger or downloaded to a computer using the software provided with the monitoring device.

Figure 7:
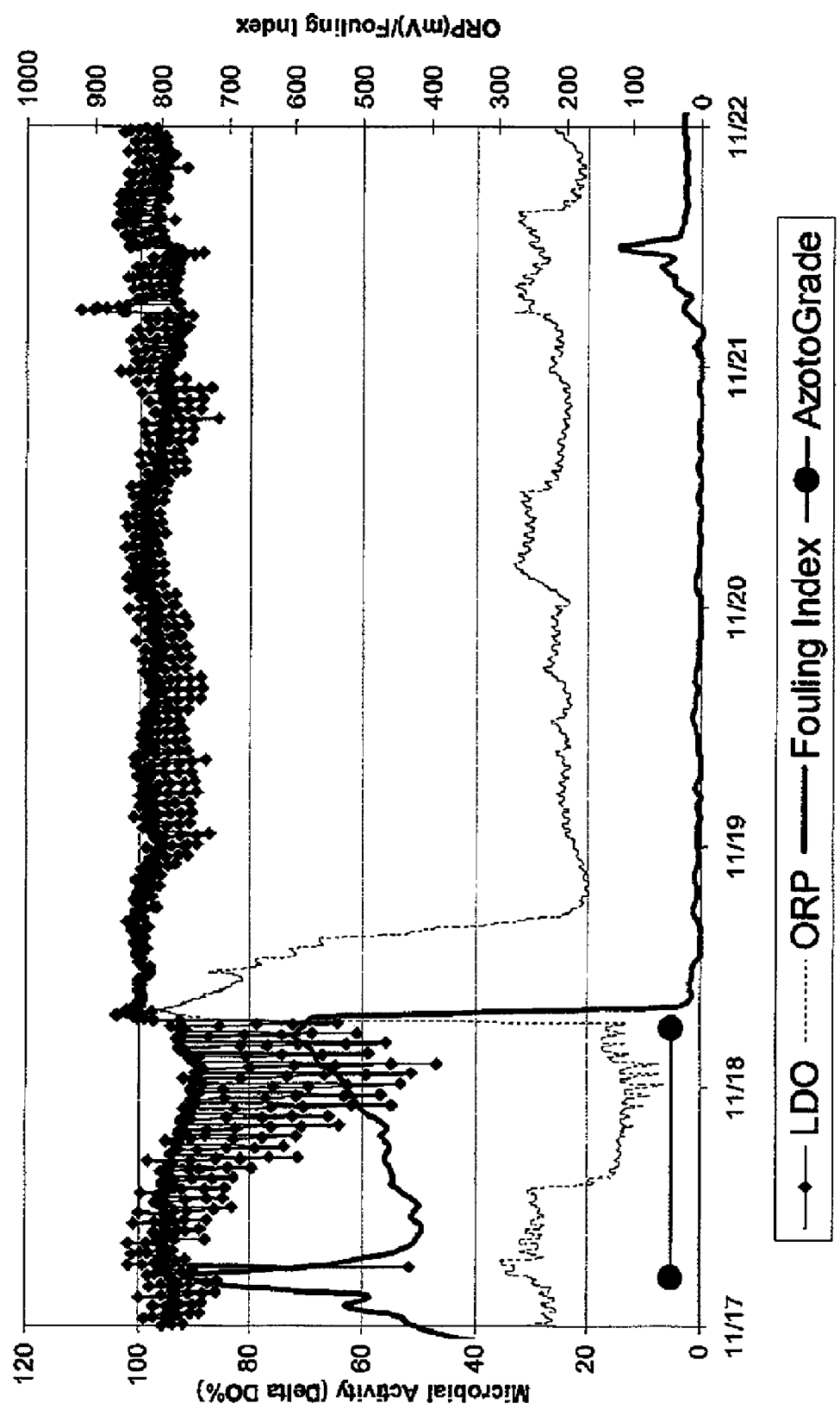
FIG. 7 shows data collected at a paper mill, which pertains to bulk (total) microbiological activity and surface-fouling.

Shortly after installing the monitoring device, process changes were immediately observed to impact the performance of the biocontrol program based on ORP measurements, microbial activity levels, and surface fouling measured with the OFM. The example provided in FIG. 7 demonstrates the impact of a change in fiber content on ORP, microbial activity, and deposition (OFM). Microbial activity is reported as LDO (% saturation) and a greater difference between the background LDO during open-flow conditions and LDO measured during stop-flow conditions indicates higher microbial activity. These data suggest that the oxidant-based program did not adequately control microbial growth and deposit formation when Azoto grade, high oxidant-demand furnish was used. Therefore, the program should be modified for improved deposit control during manufacture of this particular grade.

Example 4

The dissolved oxygen monitor measures the dissolved oxygen in the sample water continuously. The monitoring program is controlled by a PLC (Programmable Logic Controller), which will read and hold a measured LDO value until the program cycle is complete. The PLC also controls a wiper unit, which will wipe the face of the sensor clean, and a motorised ball valve, which can stop the flow of water through the sample cell.

Two basic monitoring modes are available: Bulk Microbiological Activity (BMA) Mode and/Surface-Associated Microbiological activity (SAMA) Mode. Both modes use three variables to set the program to the needs of the particular application: X, Xt and Xti. More specifically, X is the open time and closed time of the ball valve in minutes, Xt is the number of LDO readings stored during time X, and Xti is the interval between the LDO readings. While the ball valve is open and the sample is flowing the LDO readings should be stable reflecting the current state at the sample source. When the ball valve closes and the sample flow stops the dissolved oxygen in the closed off flow cell will tend to be depleted by reaction with organic material.

In BMA Mode, all the readings are taken immediately after the probe has been wiped clean. The Delta DO value provides a measure of the microbial activity in the body of the sample by reflecting the consumption of dissolved oxygen during metabolism.

In SAMA Mode the electrode is not wiped for the first part of the valve open cycle. During this time there may be a build up of biofilm on the surface of the electrode. The electrode is then wiped clean and the difference shows the level of biofilm accumulated during the first part of the cycle. When the ball valve closes readings are taken as in BMA Mode.

TABLE I

BMA Mode
X = 10; Xt = 5

| Time (minutes) | Progression | Event | Reading | Sample Flow |
|---|---|---|---|---|
| 00:00 | Start | BALL VALVE OPEN | | FLOWING |
| 01:00 | Xti − 01:00 | Wipe | | |
| 01:30 | Xti − 00:30 | Read LDO | 1 | |
| 03:00 | 2Xti − 01:00 | Wipe | | |
| 03:30 | 2Xti − 00:30 | Read LDO | 2 | |
| 05:00 | 3Xti − 01:00 | Wipe | | |
| 05:30 | 3Xti − 00:30 | Read LDO | 3 | |
| 07:00 | 4Xti − 01:00 | Wipe | | |
| 07:30 | 4Xti − 00:30 | Read LDO | 4 | |
| 09:00 | 5Xti − 01:00 | Wipe | | |
| 09:30 | 5Xti − 00:30 | Read LDO | 5 | |
| 10:00 | 5Xti | CLOSE BALL VALVE | | STOPPED |
| 11:00 | 6Xti − 01:00 | Wipe | | |
| 11:30 | 6Xti − 00:30 | Read LDO | 6 | |
| 13:00 | 7Xti − 01:00 | Wipe | | |
| 13:30 | 7Xti − 00:30 | Read LDO | 7 | |
| 15:00 | 8Xti − 01:00 | Wipe | | |
| 15:30 | 8Xti − 00:30 | Read LDO | 8 | |
| 17:00 | 9Xti − 01:00 | Wipe | | |
| 17:30 | 9Xti − 00:30 | Read LDO | 9 | |
| 19:00 | 10Xti − 01:00 | Wipe | | |
| 19:30 | 10Xti − 00:30 | Read LDO | 10 | |
| 20:00 | 10Xti | CYCLE COMPLETE | | |

MAX = Average of readings 1 > 5
MIN = Minimum reading out of 6 > 10
Activity:
BMA = MAX − MIN

TABLE II

SAMA Mode (Readings 1-7) and BMA Mode

| Time (minutes) | Progression | Event | Reading | Sample Flow |
|---|---|---|---|---|
| 00:00 | Start | BALL VALVE OPEN | | FLOWING |
| 04:30 | Xti − 01:30 | Read LDO | 1 | |
| 12:030 | 2Xti | Read LDO | 2 | |
| 18:00 | 3Xti | Read LDO | 3 | |
| 24:00 | 4Xti | Read LDO | 4 | |
| 30:00 | 5Xti | Read LDO | 5 | |
| 30:30 | 5Xti + 0:30 | Wipe twice | | |
| 31:00 | 5Xti + 1:00 | Read LDO | 6 | |
| 31:20 | 5Xti − 01:20 | Read LDO | 7 | |
| | | CLOSE BALL VALVE | | STOPPED |
| 35:00 | X + (Xti − 01:00) | Wipe | | |
| 35:30 | X + (Xti − 00:30) | Read LDO | 8 | |
| 41:00 | X + (2Xti − 01:00) | Wipe | | |
| 41:30 | X + (2Xti − 00:30) | Read LDO | 9 | |
| 47:00 | X + (3Xti − 01:00) | Wipe | | |
| 47:30 | X + (3Xti − 00:30) | Read LDO | 10 | |
| 53:00 | X + (4Xti − 01:00) | Wipe | | |
| 53:30 | X + (4Xti − 00:30) | Read LDO | 11 | |
| 59:00 | X + (5Xti − 01:00) | Wipe | | |
| 59:30 | X + (5Xti − 00:30) | Read LDO | 12 | |
| 60:00 | 2X | CYCLE COMPLETE | | |

B MIN = Reading 5
B MAX = Average of readings 6 & 7
MIN = Minimum reading out of 8 > 12
Activity:
BMA = B MAX − MIN
SAMA = B MAX − B MIN

The invention claimed is:

1. A method of measuring bulk microbiological activity and surface associated microbiological activity in a process stream comprising:

a. connecting an apparatus to a process stream, wherein said apparatus comprises a flow cell containing a plurality of openings, wherein at least one opening is a flow cell inlet for fluid drawn from said process stream and at least one opening is a flow cell outlet for fluid exiting said flow cell, a DO probe attached to one of said openings, optionally an ORP probe attached to one of said openings, a cleaning device attached to one of said openings, optionally a first conduit attached to the flow cell inlet, optionally a second conduit attached to the flow cell outlet, and a valve associated with said flow cell;
   b. drawing fluid from said process stream into said flow cell;
   c. opening the valve of said apparatus to allow fluid to be drawn into said flow cell,
   d. measuring at least once the DO concentration of said process stream with said DO probe, wherein said DO probe is not cleaned prior to each measurement;
   e. cleaning the surface of said DO probe;
   f. measuring at least once the DO concentration of the fluid inside said apparatus with said DO probe wherein prior to each measurement said DO probe surface is cleaned;
   g. closing the valve of said apparatus to prevent fluid from being drawn into said flow cell;
   h. measuring at least once the DO concentration of the fluid inside said apparatus with said DO probe, wherein prior to each measurement said DO probe surface is cleaned;
   i. calculating a Δ DO reading between step (f) and step (h) and correlating at least said Δ DO with said bulk microbiological activity in said process stream; and
   j. calculating a Δ DO reading between step (d) and step (f) and correlating at least said Δ DO with said surface associated microbiological activity in said process stream.

2. The method of claim 1 further comprising: providing an optical fouling monitor that is in communication with said process stream; drawing fluid from said process stream into said optical fouling monitor; measuring deposit formation with said optical fouling monitor; determining the type of deposits by correlating deposit formation in said optical fouling monitor with said microbiological activity determined from the Δ DO from step (i) and/or step (j) in said process stream; optionally programming a controller to add one or more chemical species to said process stream in response to said correlation between said deposition formation and microbiological activity.

3. The method of claim 1 in which an ORP probe is attached to one of said openings, the method further comprising measuring ORP in step (d), step (f), and step (h) at least one time, wherein the ORP probe is not wiped clean in step (d), optionally wherein said ORP probe is wiped clean in step (f), and wherein the ORP probe is wiped clean in step (h); optionally adding one or more oxidants to said process stream if the ORP value drops below a predetermined level; and optionally not using said DO measurements in calculating said Δ DO if said ORP value drops below a predetermined level.

4. The method of claim 1 wherein the measurements, calculations, and correlations are conducted independently of adding any nutrients to the flow cell subsequent to step (a).

5. The method of claim 1 wherein step (b) further comprises the limitation of the fluid drawing occurring such that process water openly flows from the process stream past the DO probe and then exits through the flow cell outlet.

6. The method of claim 1 wherein the fluid measured by the DO probe is reagentless process stream fluid.

* * * * *